United States Patent
Croushorn

(12) 
(10) Patent No.: US 12,295,588 B1
(45) Date of Patent: May 13, 2025

(54) ADAPTABLE PARTIAL CIRCUMFERENTIAL TOURNIQUET

(71) Applicant: Compression Works, LLC, Birmingham, AL (US)

(72) Inventor: John M Croushorn, Hoover, AL (US)

(73) Assignee: Compression Works, LLC, Birmingham, AL (US)

( * ) Notice: Subject to any disclaimer, the term of this patent is extended or adjusted under 35 U.S.C. 154(b) by 327 days.

(21) Appl. No.: 18/108,170

(22) Filed: Feb. 10, 2023

Related U.S. Application Data

(60) Provisional application No. 63/308,549, filed on Feb. 10, 2022.

(51) Int. Cl.
*A61B 17/132* (2006.01)
*A61B 17/135* (2006.01)

(52) U.S. Cl.
CPC ........ *A61B 17/1325* (2013.01); *A61B 17/135* (2013.01)

(58) Field of Classification Search
CPC .............. A61B 17/132; A61B 17/1322; A61B 17/1325; A61B 17/1327; A61B 17/135; A61B 17/1355
USPC .................................................. 606/201–204
See application file for complete search history.

(56) References Cited

U.S. PATENT DOCUMENTS

| | | | | |
|---|---|---|---|---|
| 2014/0128788 | A1* | 5/2014 | Marshall ................. | A61F 5/028 602/19 |
| 2016/0066925 | A1* | 3/2016 | van Sparrentak .... | A61B 17/132 606/203 |
| 2017/0035440 | A1* | 2/2017 | Hopman ................ | A44B 11/20 |
| 2023/0372186 | A1* | 11/2023 | Rovekamp, Jr. .... | A61F 5/05816 |

* cited by examiner

Primary Examiner — Martin T Ton
(74) Attorney, Agent, or Firm — The Gache Law Firm, P.C.; Russell C. Gache

(57) ABSTRACT

An adaptable partial circumferential tourniquet is disclosed that allows for broad application to hemorrhage sites on a human patient. The tourniquet includes a baseplate having an adaptable size with a pair of depending arms that extend lateral from each side of the baseplate. A cable and ratchet arrangement allow for the extension of the depending arms to form a semi-circumferential enclosure around a tourniquet site with the ability to cinch or constrict around the tourniquet site. A V-shaped bladder with integrated side portions expands once the tourniquet is arranged on a patient to apply pressure to tissue resulting in vasculature occlusion. Due to the unfolding segmented nature of the depending arms, the tourniquet has broad application to different body tissue sites. The based plate also includes ports, slots, and openings to allow for other medical procedures to proceed even after tightened positioning and inflation of the tourniquet.

23 Claims, 15 Drawing Sheets

ADAPTABLE PARTIAL CIRCUMFERENTIAL TOURNIQUET

FIELD OF THE INVENTION

The present invention relates generally to tourniquets. In greater particularity, the present invention relates to field dressings that utilize mechanical pressure to achieve homeostasis at the site of an injury. In even greater particularity, the present invention relates to tourniquets positioned to apply pressure on the body to stop bleeding.

BACKGROUND OF THE INVENTION

Various tourniquet devices that use a wide variety of clamping and/or pneumatic means to apply pressure to various limbs on the body have been attempted. However, prior attempts at cessation of hemorrhage from the major blood vessels of the body have not been completely successful, especially if attempted on gross battle-field wounds such as leg amputations due to anti-personnel mines or high velocity bullet percussion wounds to the lower extremities or junctional areas where the extremities meet the torso. Quite often, such wounds do not provide a satisfactory compressible site to stop arterial hemorrhages and require occlusion of the abdominal descending aorta to cut-off the blood supply to the wound in order to protect the patient's life.

However, compressing major arteries such as, for example, the abdominal descending aorta, is a difficult task. One of the major obstacles to providing an effective portable arterial tourniquet is in providing a focused compression force over the targeted area to achieve arterial occlusion. Typically, most tourniquets apply a constricting force around the circumference of a limb or over a broad area to reduce total blood flow through the limb. Such a broad application of force is ineffective to reduce or occlude blood flow through a major artery due to the typical deep location or relative inaccessibility of the artery in the body. A strong focused pressure is typically required to reach the artery to reduce blood flow. Prior inventions fail to show or disclose a technique for focusing a compression force on a major arterial vessel.

For example, U.S. Patent Application Publication No. 2007/0191881 A1 (Amisar et al.) shows a tourniquet that includes a pressure source and a selector lever attached to a CAM to facilitate manual selection of a designated pressure. This tourniquet is designed to apply pressure around a limb. There is no teaching in the patent that this device would be effectively useable for a major arterial vessel. Further, the air bladder is not a directed air bladder that would focus the compression force, but is rounded to wrap around the limb and spread the pressure force over a broad area. Such a broad application of constricting force is unusable if intended to reduce or occlude circulation through the major arterial vessel, such as the descending aorta, or for a non-compressible arterial hemorrhage in other parts of the human body such as the extremities.

U.S. Pat. No. 5,234,459 (Lee) shows an inflatable balloon for use in a tourniquet, and discloses a manual pump for inflating the balloon. U.S. Pat. No. 6,884,254 (Brooks) shows a tourniquet system that includes a lever assisted clamp means for tightening the strap around a limb. This patent is representative of a large section of the prior art that uses mechanical means, as opposed to pneumatic means, to provide a constricting force around a limb, but which fail to provide the directed compression force required to restrict blood flow through a major artery, such as the descending aorta.

More recent devices have gotten closer to providing reliable occlusion, but require a relatively high degree of experience and skill to apply the device to a patient to achieve satisfactory occlusion. For example, U.S. Pat. Nos. 8,834,517; 9,149,280; 10,751,067 (collectively, "Croushorn" or Croushorn Designs") use various types of quick connect buckles to connect a strap encircling the intended patient and various types of windlass types devices to tighten the tourniquet prior to inflating an occluding bladder. While effective, these various Croushorn Designs nevertheless require relatively precise placement of the bladder over the intended compression area and re-adjustment of the device during inflation to obtain the intended occlusion results. Moreover, the pressure must be directed to a narrow end of the air bladder and must be guided during inflation to ensure the successful application of pressure to the targeted abdominal area. In a field environment where many types of emergency response personal with varying types of experience and skill are present, successful administration of the device may require successive attempts to achieve occlusion, or if not properly adjusted may only obtain partial arterial occlusion.

Croushorn also discloses in U.S. patent Ser. No. 10/751,067 an arrangement for a V-shaped inflatable bladder (See FIG. 6) with supporting manufacturing instructions, that includes a self-stabilizing bladder lower end which is effective. The full contents of U.S. patent Ser. No. 10/751,067 are hereby incorporated by reference in this application. Nevertheless, the Croushorn Designs require a full circumferential fit around a human body, or portion thereof, in order to operate. Further, continual monitoring of the pressure exerted against a patient's body by the Croushorn Designs is required, which diverts critical attention by a heath care profession from attending to a patient's other injuries and overall condition. In addition, the complicated coordination to achieve a stable medical condition for a patient who is hemorrhaging requires multiple devices, and skillful control of those devices. What is needed is a combined hemorrhage control that combines multiple devices and, when needed, includes the potential for robotic or remote control. Moreover, there currently is no system that is capable of being both an extremity tourniquet, a junctional tourniquet, and a truncal tourniquet. Combining these capabilities into a single device would greatly simplify the training for use of such a system and assist in general deployment in the medical.

Another need in the industry is a tourniquet that includes a superior stable base that will allow for the introduction of other medical interventions such as ultrasound guided IV access, and percutaneous resuscitative interventions. Further, such a stable base would be needed to allow for remote operation or remote robotic action of such an enabled system. Finally, such a system would be superior if it could be used by medical and non-medical personnel as well as allow for robotic or remotely controlled medical intervention therapies. For example, the inventor anticipates that that such a system would incorporate the usage of advanced drone, unmanned ground military assets, and aerial military assets to broaden its usage and deployment.

The prior Croushorn Designs do not provide the above indicated advancements. Therefore, what is needed is a portable abdominal aortic tourniquet that provides the above features and structure, and that can be rapidly applied under field conditions without extensive training or skill by emergency response personnel, and which promotes the use of remote control and drone operations in treating patients in the field.

SUMMARY OF THE INVENTION

The invention is a pneumatic tourniquet that utilizes a pair of segmented arms having overlapping and articulating plate structure that surround a targeted patient site. A centrally disposed baseplate connects the two segmented arms and includes a pair of baseplate portions that may be extended away from said central baseplate to accommodate different treatment scenarios. When unfolded, the invention is partially circumferential, and uses cables that extend over and control the plate segments so that a ratcheting in the baseplate can control the size and shape of the semi-circumferential tourniquet. A bladder affixed to the underside of the baseplate extends downward when inflated and is V-shaped so that a lower edge of the bladder may apply focused pressure on a targeted patient site. In addition to a primary shaped bladder, a pair of elongated side bladder portions extend underneath the plate segments on each side of the segmented arms so that precise automated control of the size and shape of the tourniquet may be accomplished. As such, the tourniquet may be used on both large and small portions of the human body.

Other features and objects and advantages of the present invention will become apparent from a reading of the following description as well as a study of the appended drawings.

BRIEF DESCRIPTION OF THE DRAWINGS

A tourniquet incorporating the features of the invention is depicted in the attached drawings which form a portion of the disclosure and wherein.

DESCRIPTION OF THE PREFERRED EMBODIMENTS

Figure 1:
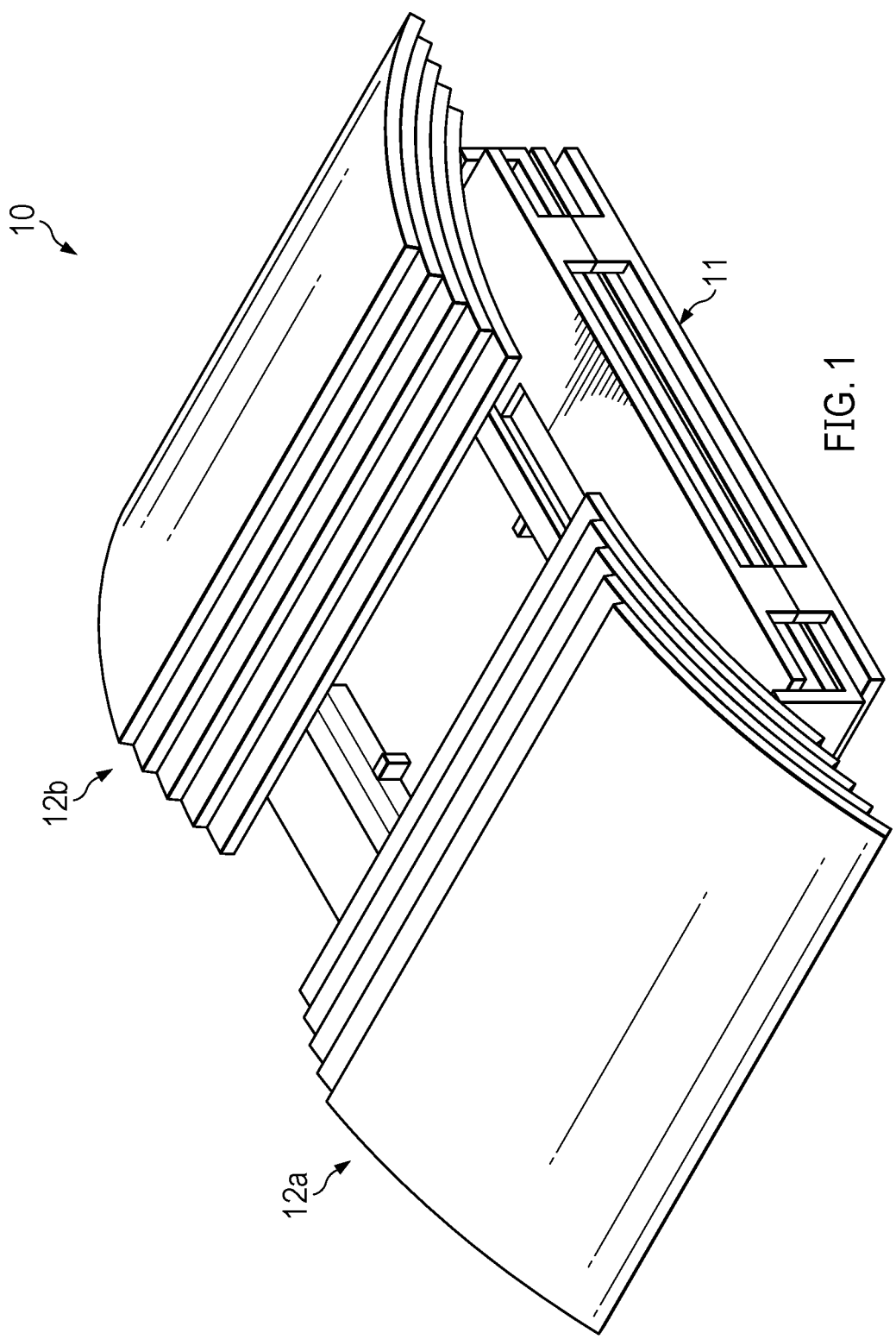
FIG. 1 shows a perspective view of an adaptable partial circumferential tourniquet in a collapsed state according to the present invention.

Referring to the drawings for a better understanding of the function and structure of the invention, FIG. 1 shows an overview of the invention 10 in a collapsed state ready for deployment. The invention includes a mechanical expandable baseplate 11 supporting left and right, curved extensions 12a,b. Left and right extension portions 12a,b include a plurality of connected, articulating plates that are extendable from the portrayed folded or collapsed state into an expanded state. The lateral portions 12a,b are also controlled by a central ratcheting mechanism 17 as will be discussed. The shown collapsed configuration allows for compact storage of the invention as an emergency medical kit and is mostly constructed of light-weight plastic components to reduce weight. All components are manufactured by well-known manufacturing techniques, such as injection molding plastic processes or stamped metal fabrication.

Figure 2:
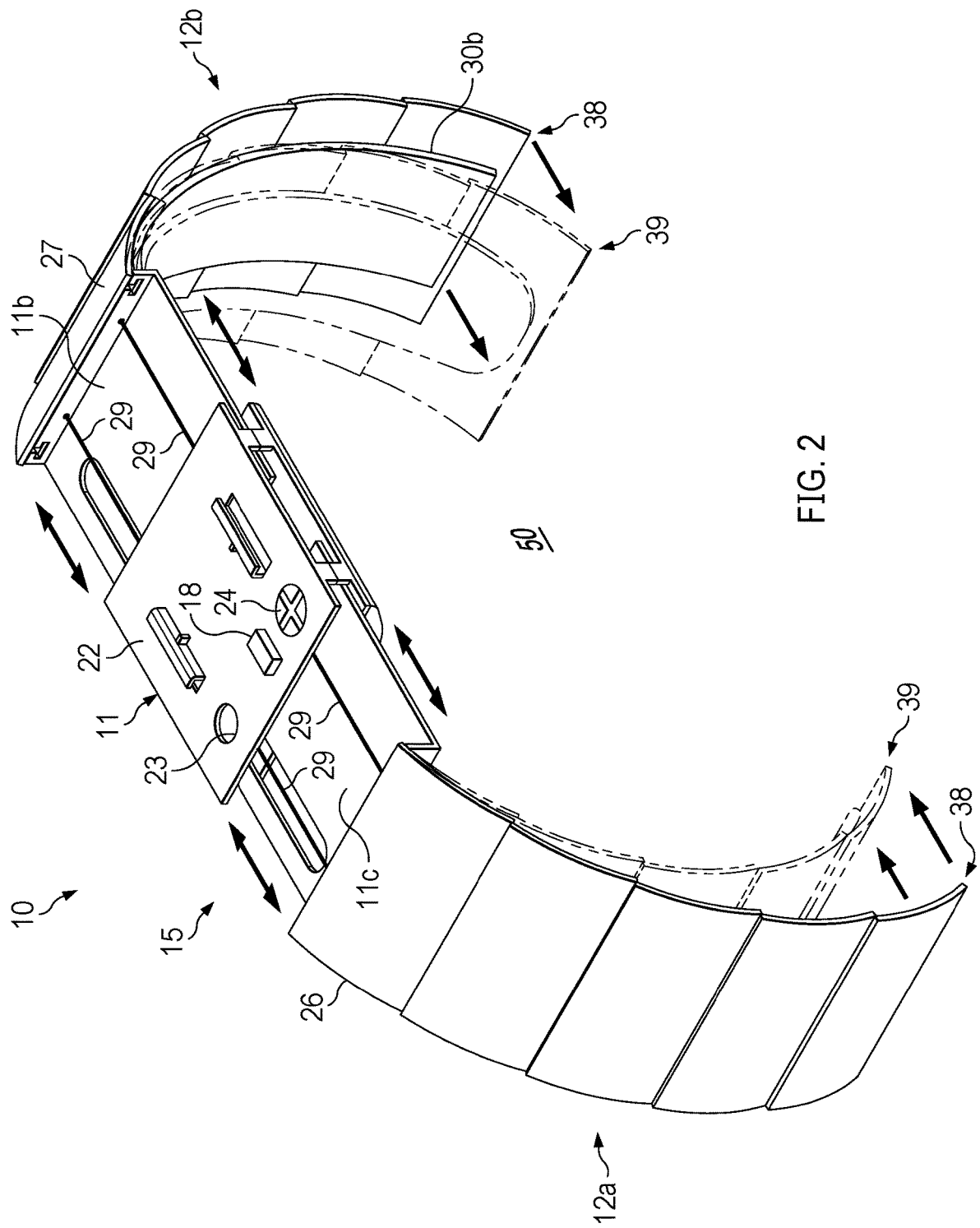
FIG. 2 shows a perspective view of the invention in an expanded state ready for deployment on a patient.

Referring to FIG. 2 baseplate 11 supports curved arm extensions 12a,b that depend downward and away from each lateral side of baseplate 11, with each arm extension consisting of a plurality of identical segments 26 (left side) and segments 27 (right side), starting with first portions 26 and 27 as shown. As shown, baseplate 11 is configurable to allow for lateral expansion 15 of inner plate portions in baseplate 11 to allow the invention to adapt to differing treatment scenarios. Arm portions 12a,b form a circumferential portion of invention 10 on each side of baseplate 11 is that wraps around a portion of a patient's body for which the tourniquet 10 is targeted. A ratcheting mechanism 17 (see FIG. 4B) is held within baseplate 11 and may be manipulated, either manually or with a servo-initiated actuation device, to cause the curved extension portions 12a,b to be drawn around the targeted portion of the patient such that the tourniquet invention is compressed toward a center point 50 and around the surface of the patient, thereby providing a stable interior surface and platform into which an internal bladder 30 may be inflated.

Figure 3A:
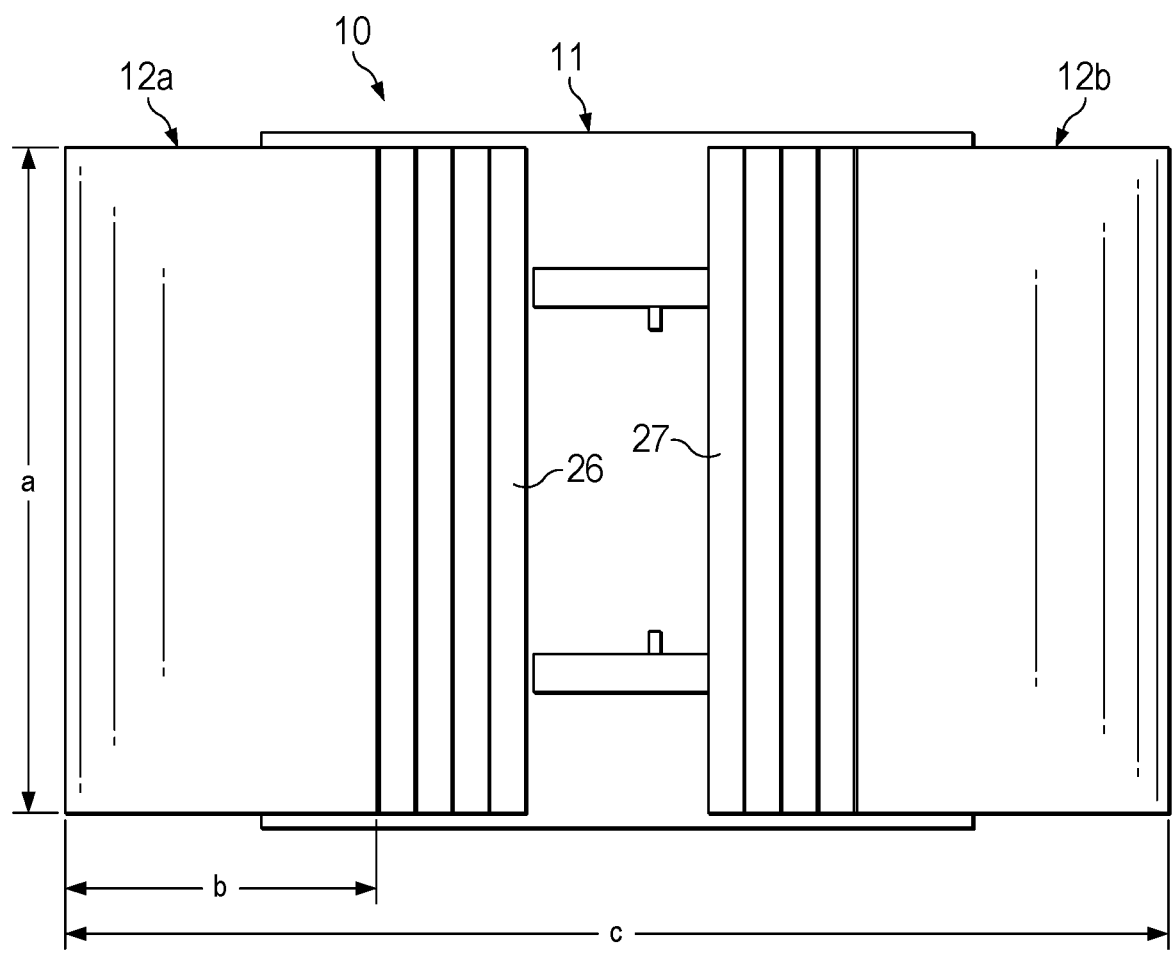
FIG. 3A shows a top plan view of the invention.
Figure 3B:
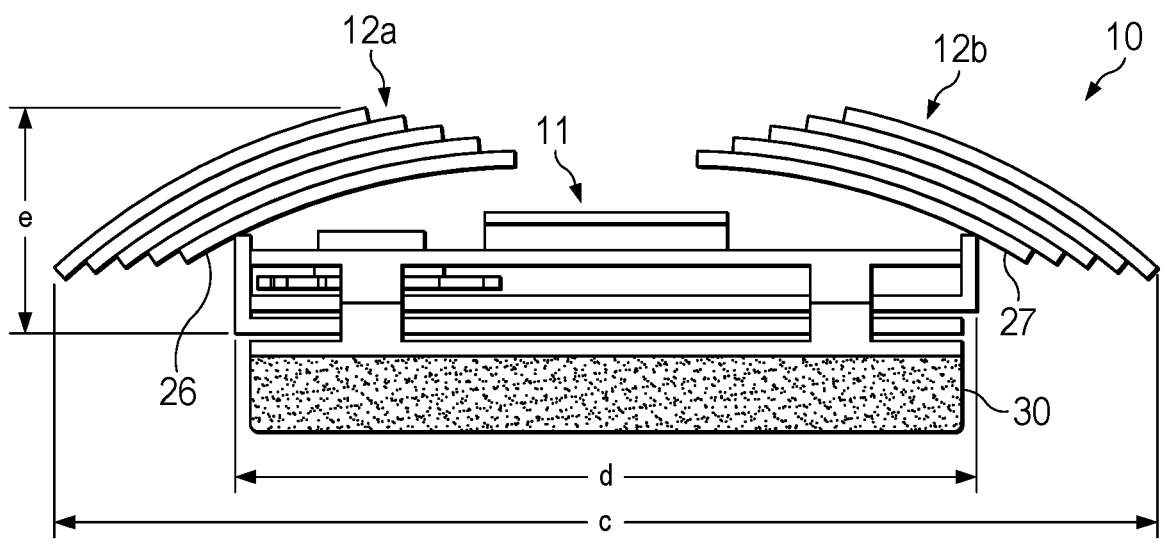
FIG. 3B shows a side elevational view of the invention.

As shown in FIGS. 3A and 3B, the tourniquet 10 has preferred dimensions of height (a) of 11.2 cm, a bilateral, collapsed segmented portion (b) of 8 cm, and an overall length (c) of 30.4 cm. The baseplate 11 with a nested segment portion has a height (e) of 3.2 cm, not including the height of a bladder 30 (side portions 30b,c not shown), and has a width (d) of 11.2 cm in a non-extended state. Hence, the invention when collapsed for storage has a substantially compact shape.

Figure 4A:
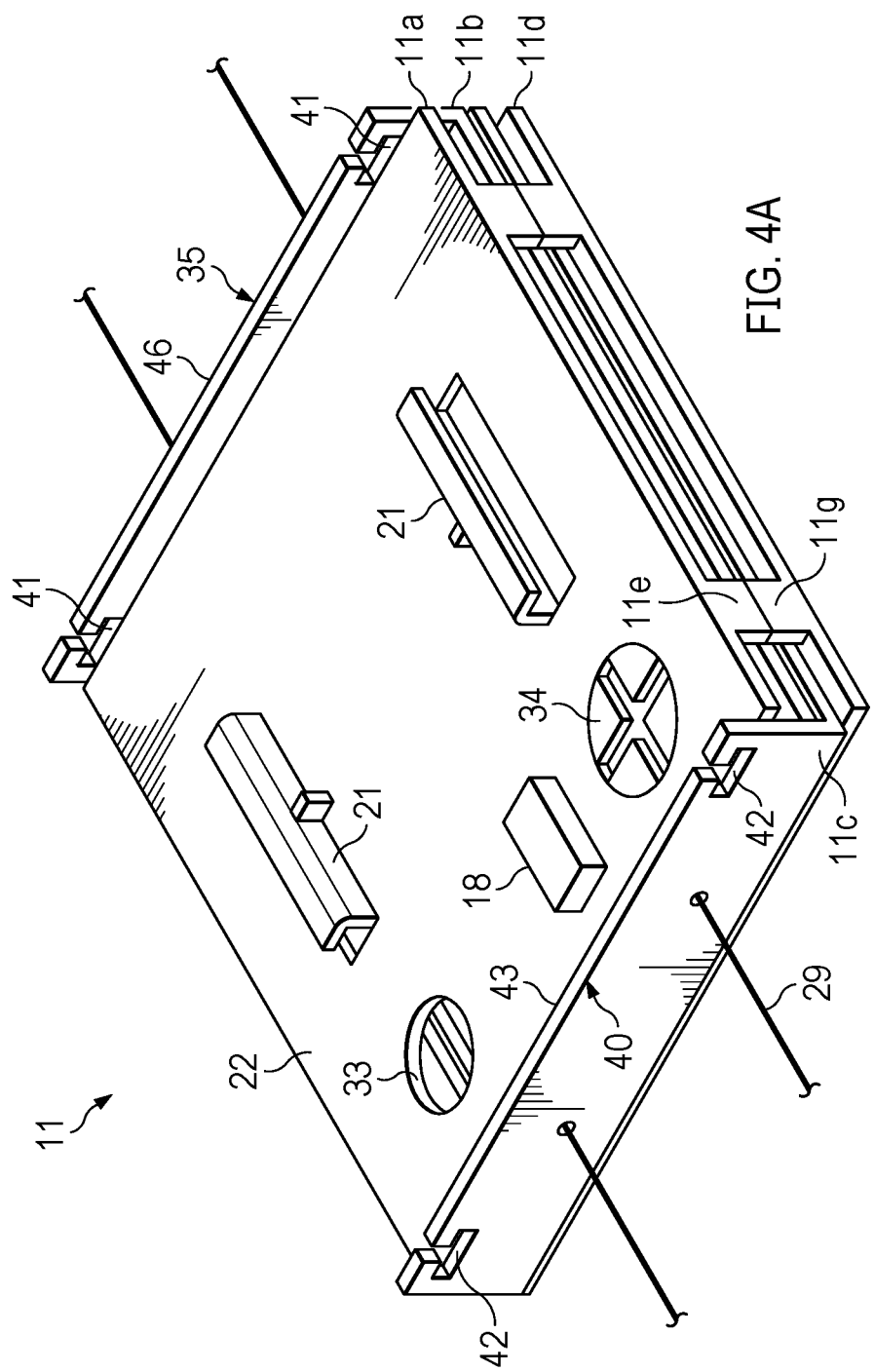
FIG. 4A shows a magnified view of the tourniquet baseplate.
Figure 4B:
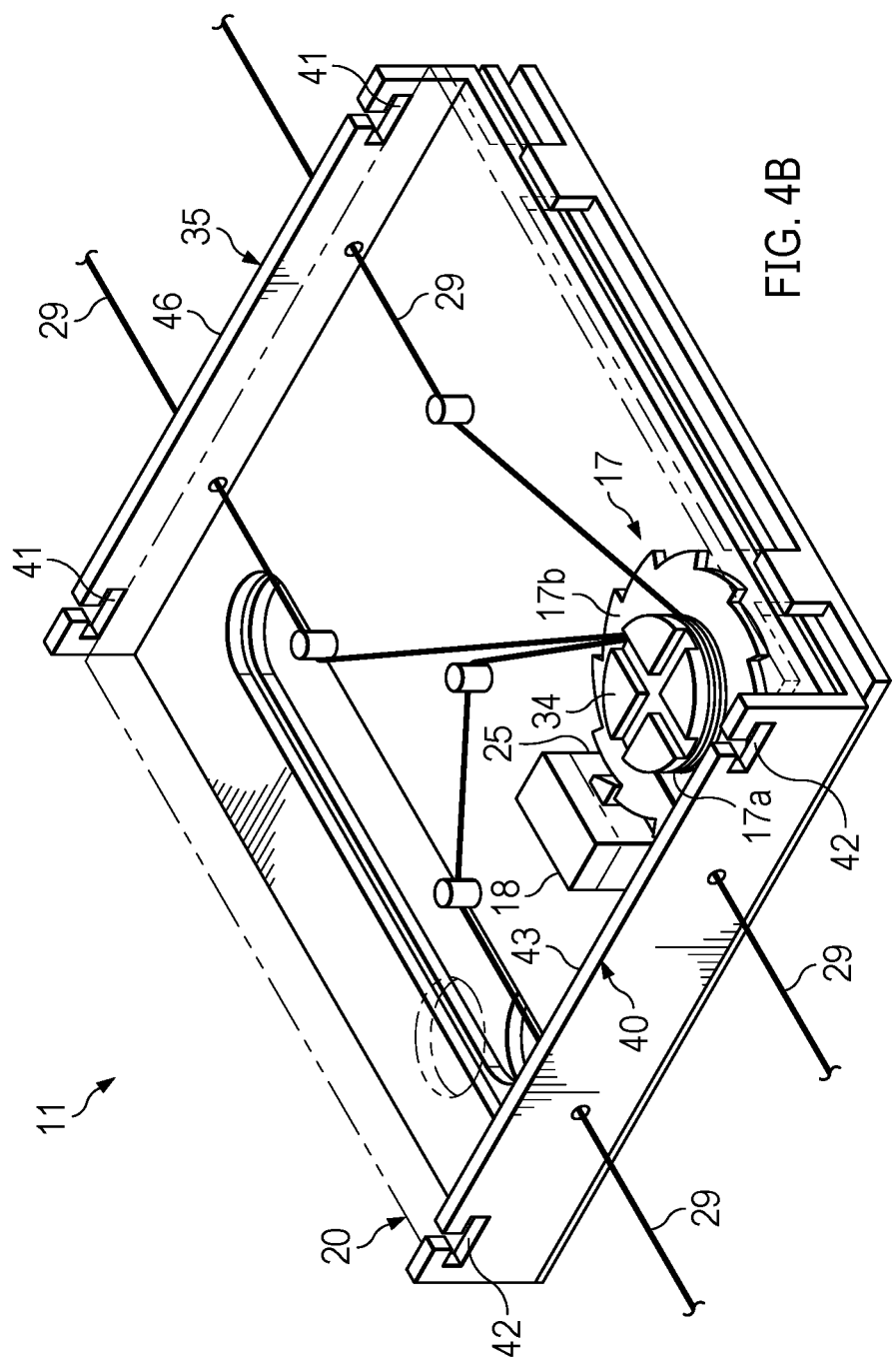
FIG. 4B shows a magnified detail view of the ratcheting control spool.

Referring to FIGS. 4(A-B) and 5, expandable baseplate 11 includes a top surface 22 that defines two attachment points 21 for medical diagnostic sensors and various instruments to monitor the patient's vital signs, and to generally provide access to a patient's underlying tissue. Top surface 22 also includes a tubing port 33 and a ratcheting gear access opening 34. Under top surface 22, baseplate 11 includes a rotational hub 17a that holds a ratchet gear 17b within base 11 and allows ratchet 17 to freely rotate. The ratchet 17 acts as a wire spool that holds a portion of flexible wire or cable 29 that is used to cinch or circumferentially collapse left and right extension portions 12a,b to conform expanded arms around a targeted tourniquet area. Essentially, cable 29 operates as a control mechanism for controlling the circumferential conformance of tourniquet 10 in relation to the targeted body surface.

Referring again to FIG. 2, it may be seen that control cables 29 are embedded within and along the inner surfaces of portions 12a,b partially defining a portion of internal bladder 30. When tightened with ratcheting mechanism 17, cables 29 circumferentially collapse side portions 12a,b from a relaxed or expanded position 38 to a constricted position 39 as shown. A release button 18 is included on the baseplate 11 upper surface 22 and retained in position with a dual position movement via retention clip 25 affixed to underside 20 to release tension in the ratcheting mechanism and to the curved extendable arm plates, as well as a lock on the expandable baseplate. When the release button is actuated, the tourniquet returns to a loose and manipulatable state so that the tourniquet 10 may be easily removed from a patient's body for decontamination and cleaning.

Figure 5:
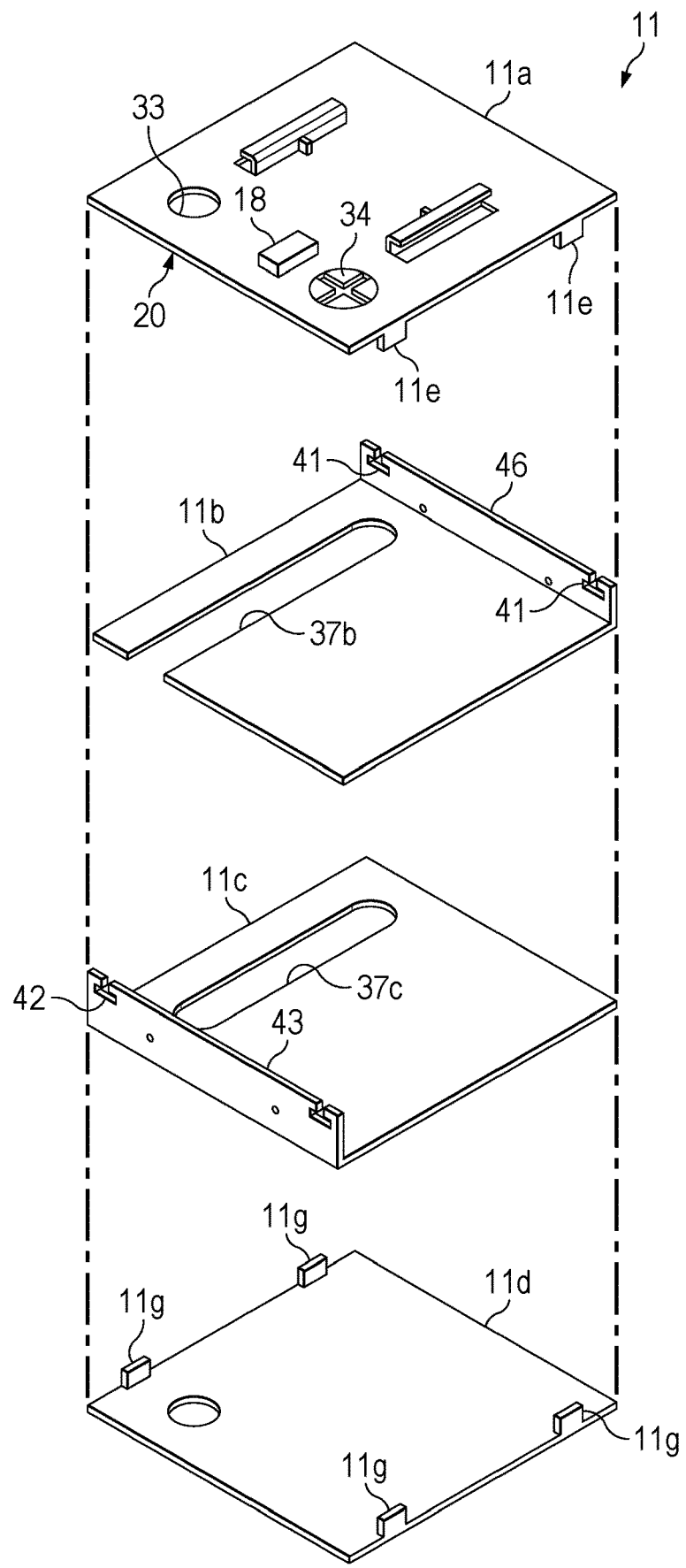
FIG. 5 shows an exploded view of the tourniquet baseplate.

FIG. 5 shows an exploded view of the baseplate 11 having four plate portions 11a-11d. Portion 11a includes upper surface 22 and lower surface 20 along with previously mentioned cut outs 33 for air tubing and a ratcheting gear connector 34 to tighten cable ratchet system 17. A right sliding plate 11b bears against underside 20 of upper portion 11a and includes a raised lip 46. Sliding plate 11b is supported by a left sliding plate 11c in slidable engagement via slot 37b and includes a raised lip 43 that acts as a stop to right plate 11b. Similarly, slot 37c on plate 11c acts as a stop to plate 11b. Lower portion 11d slidably supports left plate 11c and aligns movement of both plates 11b and 11c via attachment points 11g which also act as gripping tabs between top plate 11a and bottom plate 11d such that plates 11a, 11b, 11c, and 11d are sandwiched together into a unified whole. Plates 11a and 11d are sized such that interior plates 11b and 11c may move in laterally directions, thereby allowing for the conformity of baseplate 11 to fit the targeted tourniquet area and form a stable platform from which side arm portions 12a,b may be deployed. As may be understood, side extension portions may be pulled out from baseplate 11 through manual manipulation prior to constriction via cable ratchet mechanism 17 to fit various treatment scenarios.

Lower portion 11d of baseplate 11 includes two pairs of internal guide grooves on its upper surface (not shown) to which sliding plates 11b and 11c are slidably anchored. Also shown are cut outs for the inflation tubing 23 and ratcheting gearing access 24 from top portion 11a. As can be seen, left and right extensions 11b and 11c extend outwards but include features to retain adjacent side segments 26,27 on arms 12a,b. In particular, each lateral distal edge of plates 11b and 11c include features for slidably connecting the top most segmented plates 26,27 of segmented arm portions 12a,b, to allow for nesting of the first two segments 26,27 over top portion 11a when in a folded, collapsed condition. An upper portion 35,40 of each plate 11b and 11c include two T-shaped guides or grooves 41,42 formed therein to allow for slidable retention of first side segments 26,27 so that each subsequent lateral side segment may slide over the top of plate portion 11a. Each subsequent segment repeats an identical structure to allow slidable retention and overlapping of each consecutive segment in arms 12a,b.

Figure 6A:
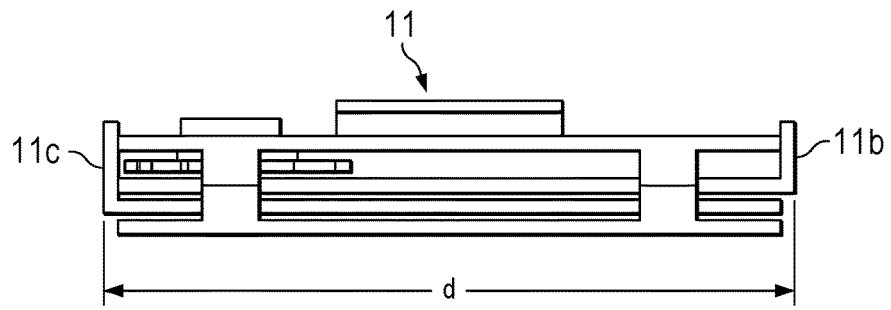
FIG. 6A-6C shows three diagrammatic views of the tourniquet baseplate laterally expanded to adjust to different treatment scenarios.
Figure 6B:
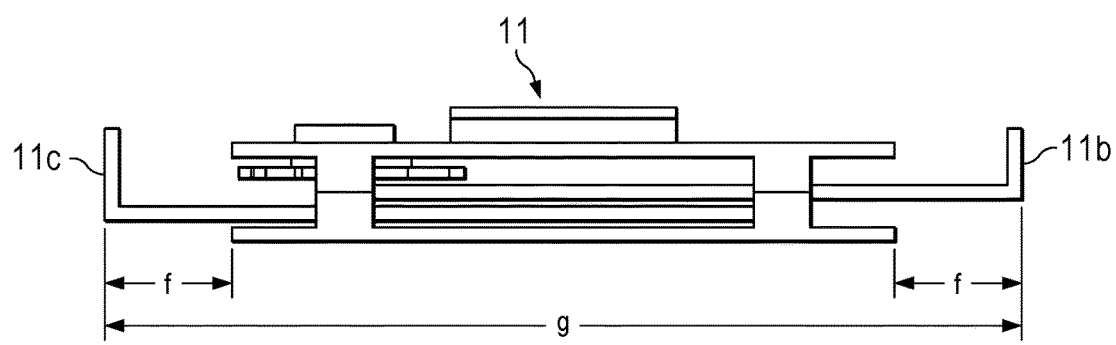
Figure 6C:
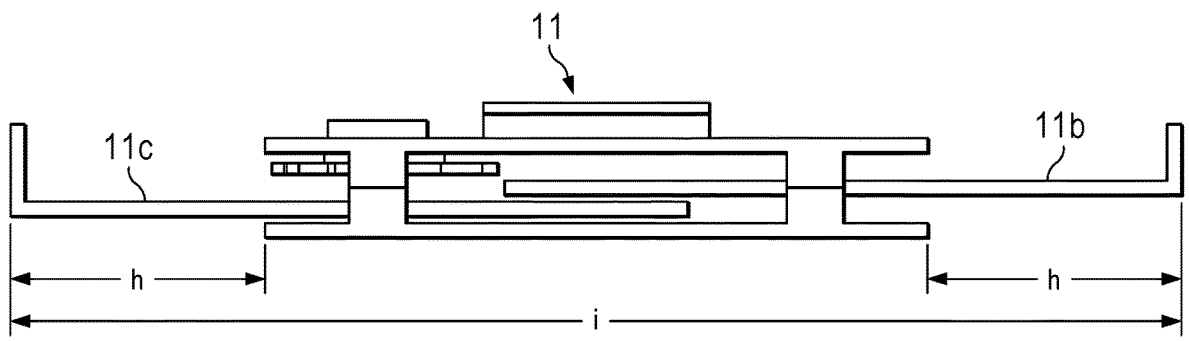

Referring now to FIGS. 6A-6C, baseplate 11 may be reconfigured to expand or extend for different treatment scenarios. FIG. 6A shows baseplate 11 un-extended in which width (d) comprises the collapsed state previously shown in FIG. 1. This state is typically adapted to be used on smaller extremities such as upper or lower arm portions of a human patient. FIG. 6B is a partially extended position or state in which expansion dimensions (f) on each side of plate 11 comprise about 2 cm each, leading to an overall expanded width of approximately (g) 15.2 cm. The position shown in FIG. 6B is contemplated to be used with larger extremities of a human patient, such as upper or lower leg locations. The state or position shown in FIG. 6C is contemplated to be used for torso applications in which the bladder penetration provides for targeted occlusion of interior blood vessels, as will be further discussed. This state comprises a fully expanded position of baseplate portions having, for example, lateral expansions of (h) 4 cm and an overall width of (i) approximately 19.2 cm.

Figure 7A:
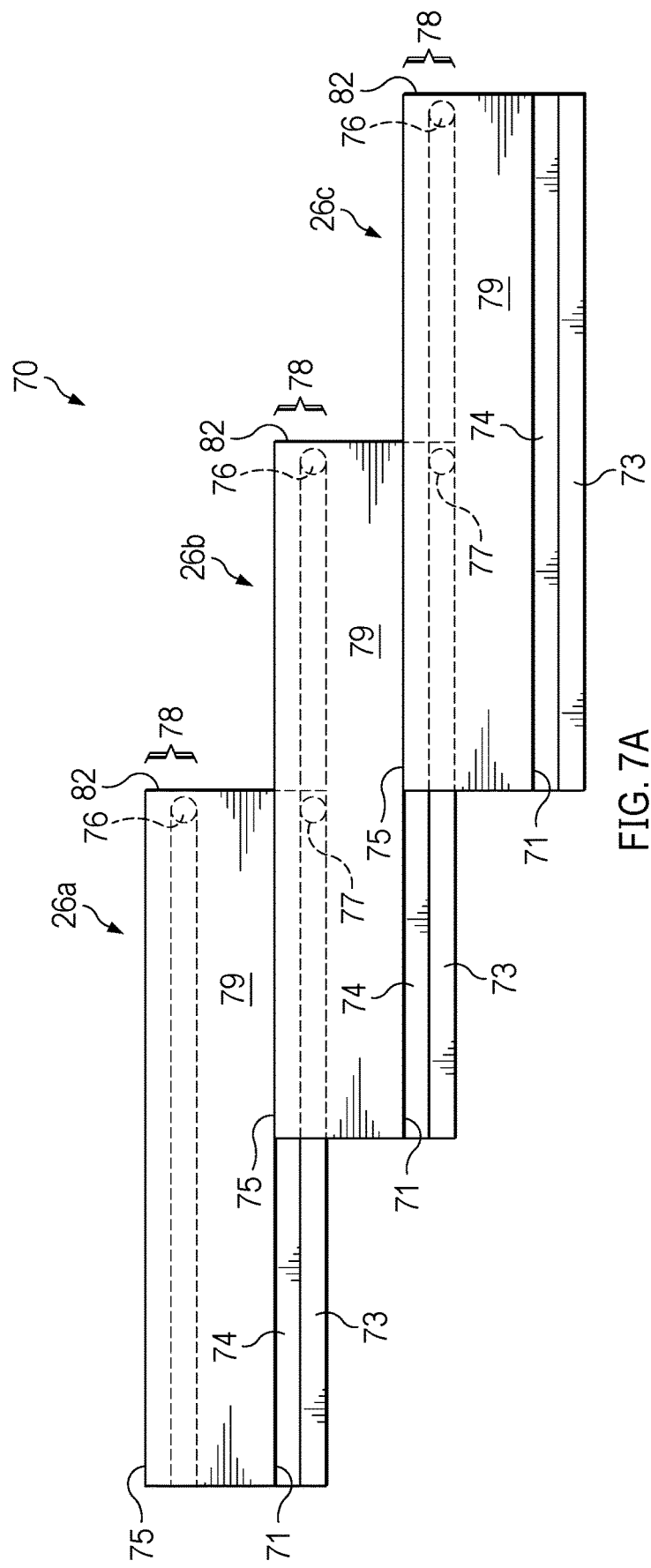
FIG. 7A shows a view of several plate segments connected to one another in a partially nested state.
Figure 7B:
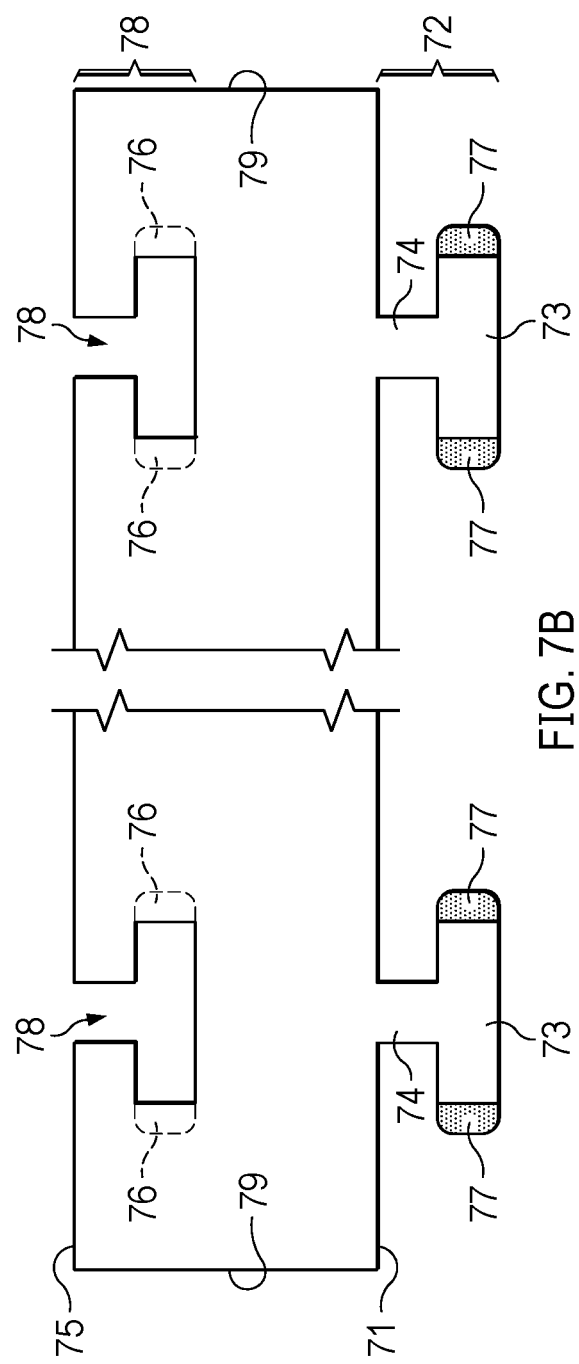
FIG. 7B shows an end view of a segment.
Figure 7C:
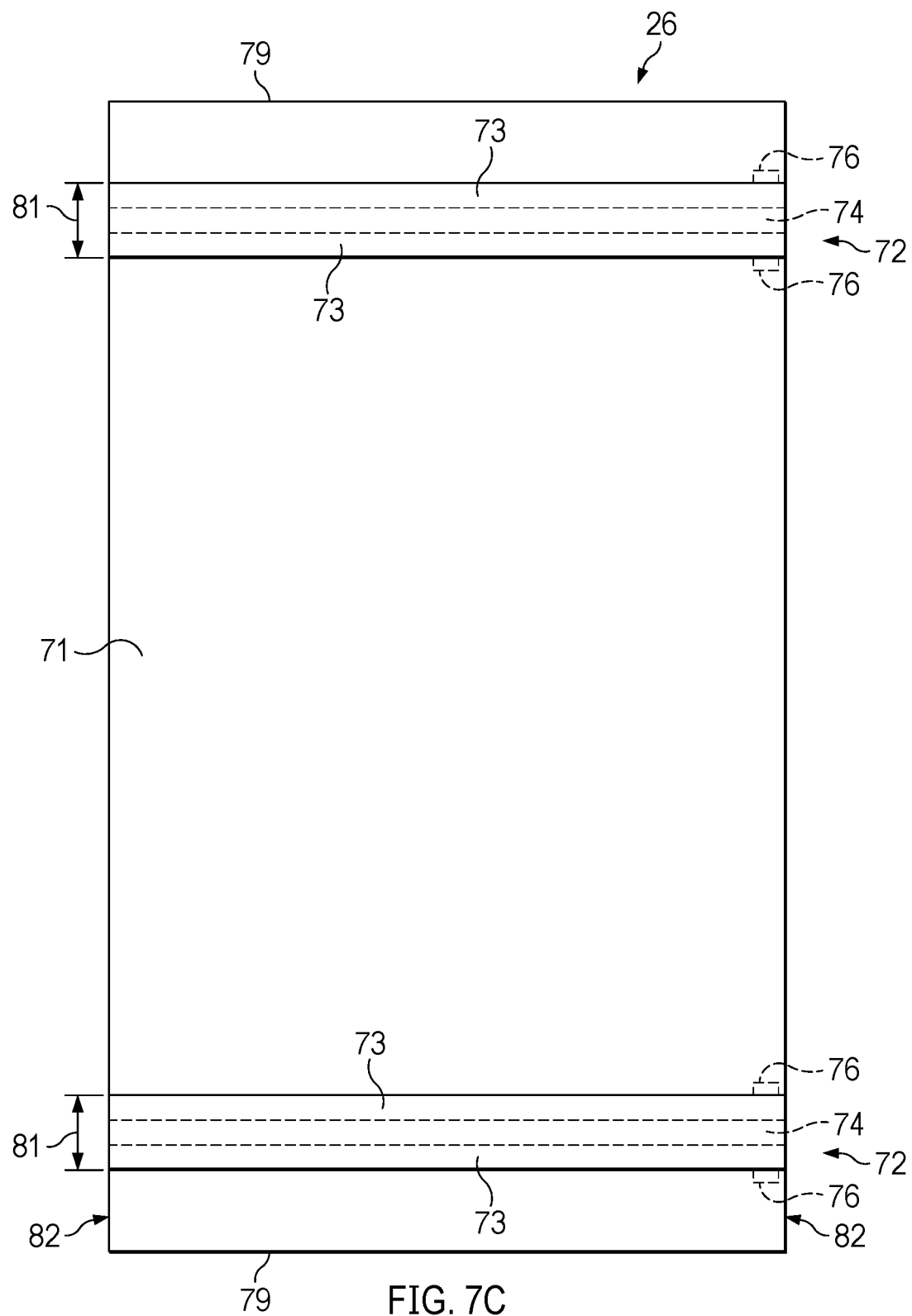
FIG. 7C shows plan view of the lower surface of a segment showing the depending pair of guide rails.

FIGS. 7A-7C and FIG. 8 show how each plate segment 26,27 are joined to one another and to baseplate 11. Each left and right extendable baseplate portions 11b and 11c include a pair of slots or grooves 41,42 on raised lip portions 35,40 cooperatively sized to receive a pair of rails formed on the underside of each plate segment 26,27. This allows each first lateral segment plate to be slidably affixed to the baseplate 11 and allows for each first lateral segment plate to be slid over the top of baseplate 11 when in a collapsed state as shown in FIG. 1. Each lateral segment 26,27 further includes a pair of grooves or slots formed on their upper surfaces. Subsequently, segment plates extending along arms 12a,b all have the same configuration so that each adjacent segment may be inserted into the slot of an outwardly positioned, adjacent segment. A portion of arm 12a is shown in FIGS. 7A-7C with three connected segments 26a-26c, with each segment partially overlapping and connected together to form a 3 segment partially nested group 70. Each segment includes a pair of rails 72 extending downward from the lower surface 71 of each segment. A cooperatively sized slot 78 is formed within each segment such that each pair or rails 72 may be inserted into a below positioned slot 78 of an adjacently positioned segment. For example, segment 26a can be connected to segment 26b and segment 26b can be connected to 26c, and so on, to build left or right arm portions 12a,b of apparatus 10 shown in FIG. 2. Each rail 72 is T-shaped with a top head width 81 supported by a stem 74 with the head 73 spaced away from the lower surface of each segment. The body of segment 26 defines a cooperatively sized slot 78 having an inner head width substantially the same as width 81, but with sufficient space maintained between the two to allow free sliding movement of rails 72 within slots 78. One end of each rail 72 further includes a lateral extension portion 77 that extends outwardly from the end of each rail so that as the end of each rail meets the end of a slot into which it has been inserted the extension 77 contacts and retains the adjacent segment end 82 in close proximity to an adjacent segment end 82. In addition, each groove 78 has formed within each end of the groove a sized stop 76 that receives and holds extension portion 77. Preferably, extension 77 is substantially rounded and stop 76 is cooperatively curved to receive extension 77 and allow limited rotation of each segment end 82 relative to an adjacently positioned segment. This arrangement allows for each arm 12a,b to be freely extended away from or retracted toward baseplate 11 and allows for some flexibility of each segment within each arm 12a,b. The arraignment also provides for some positioning leverage to assist in contraction and compression of arms 12a,b.

Figure 8:
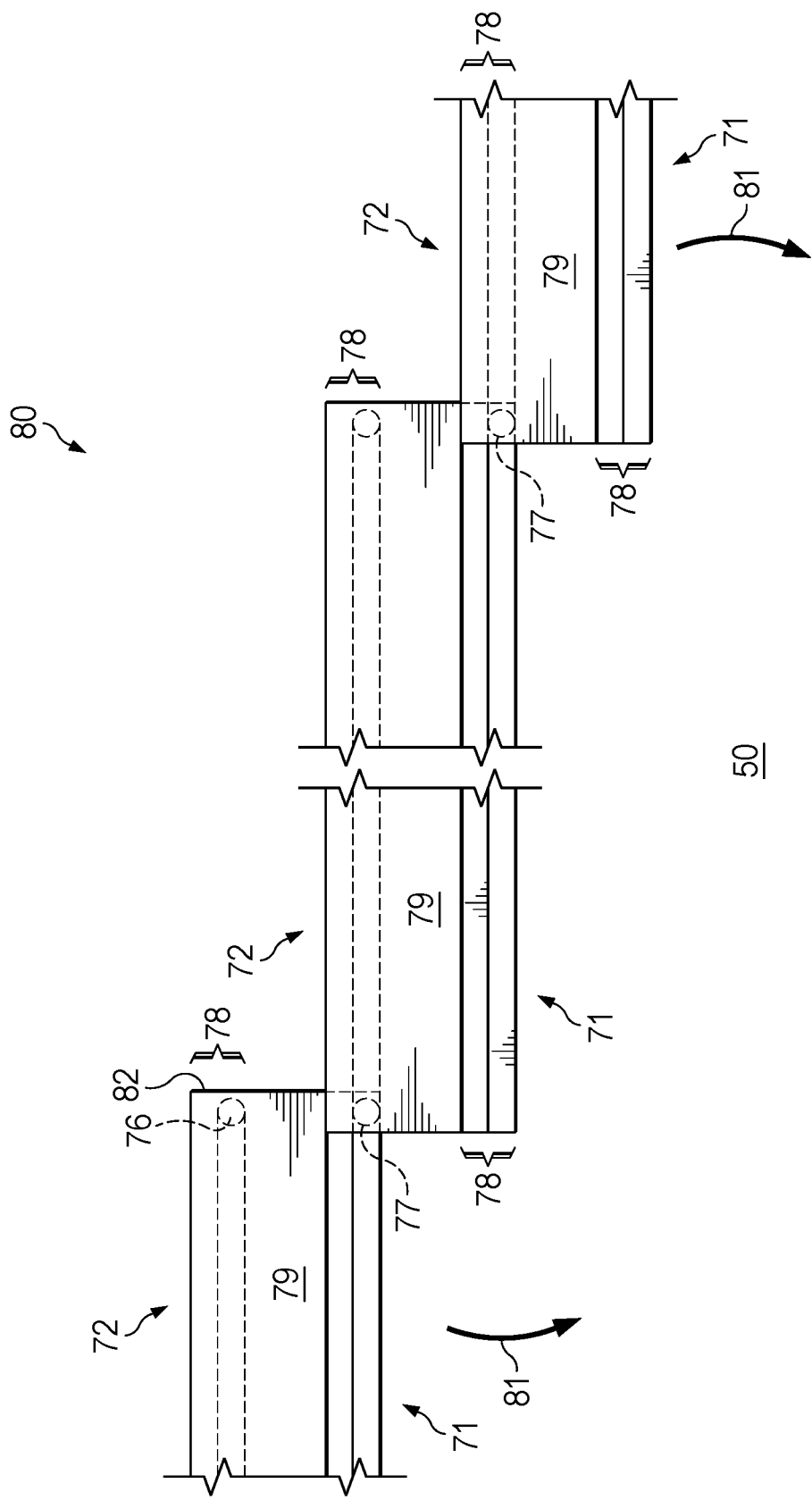
FIG. 8 shows an elevational view of three plate segments connected to one another in a fully expanded state.

As further shown in FIG. 8, when in a fully expanded state 80 each segment 26 (27 for right arm 12b) has its extension portion 77 seated within stop 76. In this expanded state, segments 26 (27 for right arm) may rotate inward 81 toward center position 50 (see FIG. 2) so that as cable 29 is drawn up with ratcheting mechanism 17, segments 26 (27 for right arm) rotate inward to assert force on a targeted treatment area for a patient. The configuration further resists outward arms 12a,b from mechanically rotating away from central point 50.

Figure 9:
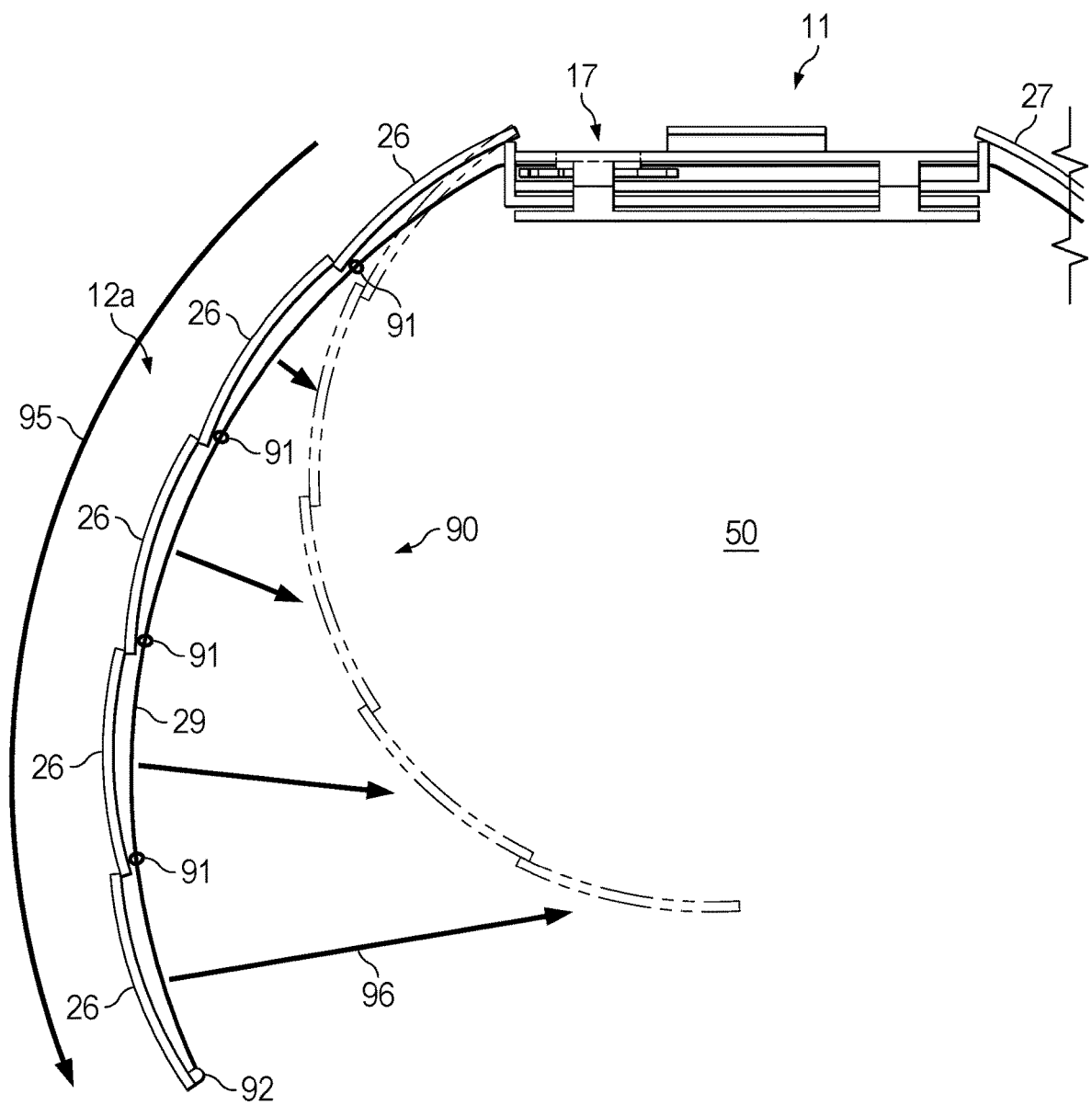
FIG. 9 shows a perspective view of one depending arm of the tourniquet showing the integrated compression cable.

Referring now to FIG. 9, it may be seen a cable retraction system 90 having in one embodiment a pair of cables 29 that runs along the underside 71 of each arm portions of 12 and spaced approximately 20% away from the edge 79 of each segment 26 (27 for right arm). Each cable 29 is similarly spaced from the underside 71 through a series of guides 91 that are equally spaced along the path of the cable 29 to prevent cable 29 from lateral movement underneath each segment 26 (27 for right arm), but allow free movement through each guide 91. For example, in its simplest form, an eye hook could serve as a cable guide, although various types of retention elements may be satisfactorily used. The cable 29 ends in a terminus anchor 92 that secures the cable at its furthest extent along arm 12a (12b for right side). As will be understood, ratchet 17 held by base 11 includes internal guide paths (see FIG. 4B) within base 11 so that cable wire 29 may be routed within base 11 and around a ratchet spool 17. As the ratchet 17 is wound or unwound the cable 29 responsively is either retracted or loosened equally in each cable simultaneously. When retracted, force is applied along guides 91 once slack from terminus anchor 92 is removed. Because each guide is spaced from the underside 71 of each segment, and because an arcuate path 95 is formed along arm 12a, the retracted wire forces the segments 26 inwards 96 in order to lessen the distance along path 95. This is similar to the way that a human limb works by pulling inwards at key points along a bone path to force closing of the arc inwards a central point.

In an alternate embodiment, each segment may integrate a guide path internally within each segment with each segment having formed within it a tunnel extending from one end to another along arm path 12a, thereby and replicating the guide path formed with cable guides. In this alternate embodiment, the compressive arcuate leverage 96 exerted along path 95 towards center point 50 may be reduced because the tunnels are not set-off from the underside 71 of each segment to the extent of the retention guides 91 embodiment. However, this can be addressed by optimizing the shape and position of the internal rail stops 76 to allow for movement of each distal end of each segment to be positioned slightly inwards relative to the position of the proximal end of each segment, thereby creating a slight inward cant of each segment at each distal end.

Figure 10:
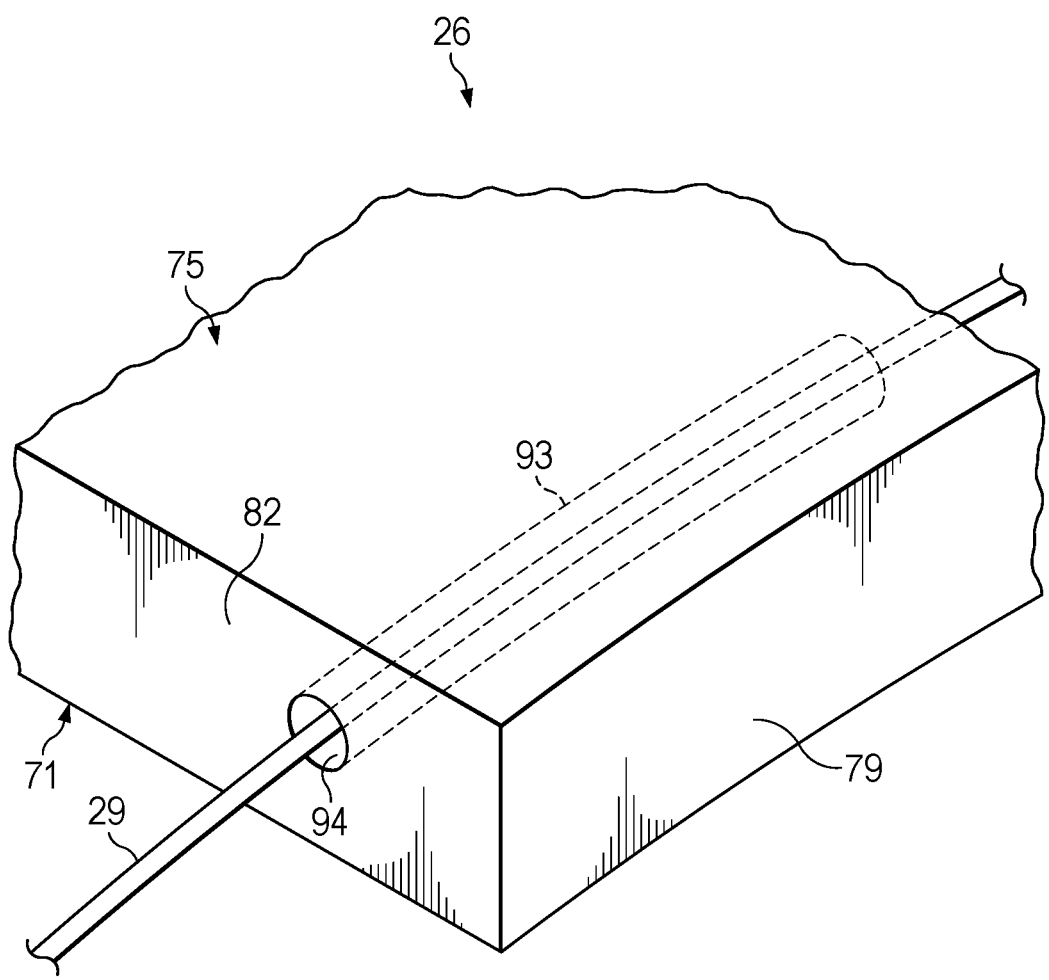
FIG. 10 shows an alternate embodiment of the compression cable guide path.

FIG. 10 shows a detailed view of this second embodiment just described. Each segment 26 includes formed inside, through injection molding or a similar manufacturing technique, a pair of tunnels 93 extending along each segment and having their ends 94 open at each end 82 of each segment. The tunnel positions are identical in each segment such that each tunnel opening 94 is closely matched the an adjacent position of an adjoining segment tunnel opening 94. This forms an unbound arcuate path 95 for cable 29. In this embodiment, terminus anchor 92 may be achieved with a simply end screw within the tunnel end of the last segment to secure the cable inside the last tunnel at the most distal point in the most distal segment.

As may be understood, cable 29 may consist of two parallel separate cable arcs along path 95 with a final terminus anchor 92, or cable 29 may flow continuously down one side of path 95, around the end 82 of the most distal segment 26, and back up the other side along the same cable path, thereby obviating the need for a terminus anchor and creating a continuous movement of cable 29 along path 95. This creates a system such that as the cable is drawn up by ratchet 17, the cable is able to freely move around path 95 down and then up segment arm 12a, similar to a simple medieval style bag purse with a draw string closure.

It will be understood that segment arm portion 12b will work in an identical fashion to arm portion 12a, and ratchet 17 may be directed through internal cable path guides in base 11 to allow for simultaneous and equal retraction of cable 29 in both arms 12a,b so that the contraction of one arm will create an equal compressive force in the other arm. The arrangement results in actuation of ratchet 17 forcing the rotation of both arms 12a,b moving them toward a center point 50 simultaneously and yielding a substantial compressive force around a targeted tourniquet location on a patient.

Figure 11:
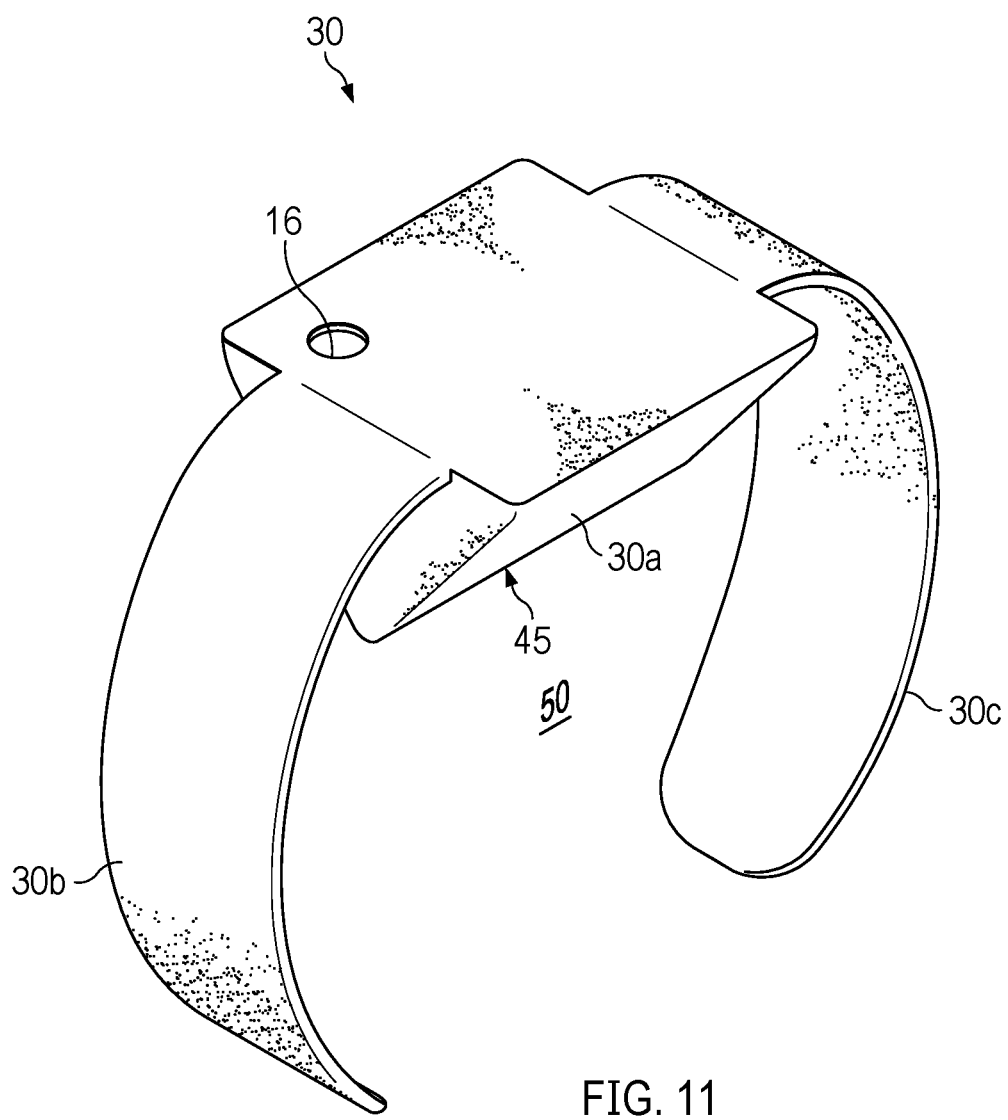
FIG. 11 shows a perspective view of the internal bladder extending underneath the articulating segmented plates in the invention; and, FIG. 12A shows the tourniquet in an expanded circumferential placement sized to surround a targeted patient area; and, FIG. 12B shows the tourniquet side plates in a compressed state with the bladder inflated to compress a targeted area on a patient.

FIG. 11 shows a bladder arrangement 30 with V-shaped bladder portion 30a that extends downward from baseplate 11 toward a focused target point 50, which would presumably be co-located with a targeted body portion on a patient. Extending on each side are elongated side bladder portions 30b,c that are fluidly integrated with large central bladder portion 30a. Side bladder portions 30b,c are thinly formed to be affixed to the underside 71 of each segment along extendable arms 12a,b along path 95 in a manner that allows the extension of arm portions 12a,b around the top exterior of side bladder portions 30b,c. As will be understood, cable 29 is slidable affixed to guides 91 and bladder portions 30b,c are affixed to underside 71 so that as arms 12a,b are expanded or contracted side bladder portions 30b,c will be retained against the underside of each segment while allowing for bladder and segments 26,27 to accordion together up and over base 11. The arrangement allows for the expansion of side portions 12a,b around a targeted body area manually, and then engaging constriction conformity around the targeted body area by cinching cable 29. Integrated bladder 30 may then be inflated to provide compression on patient tissue and force tissue displacement to compress underlying organs and vasculature. Inflated side portions 30b,c provide additional support and vasculature constriction around bladder tip 45 to assist in occlusion of damaged arterial tissue. Bladder 30 may be inflated by a hand bulb 31 (not shown), or alternatively by a remotely operated internal servo pump that includes internal sensors to sample internal bladder pressure and respond to pre-programmed firmware or a remotely programed set of values from a remote operator. An inline manometer 14 (not shown) allows for visual monitoring via a local operator or technician of bladder air pressure, and a one-way valve with port 32 controls air into bladder 30 via insufflation port 16. The wedge-shaped portion 30a of bladder 30 includes a lower tip 45 that should be positioned against a patient's targeted area such that upon inflation of bladder 30 tip 45 penetrates into the tissue to cause vasculature compression to stop acute hemorrhaging (i.e. achieve vascular occlusion/vascular homeostasis).

Figure 12A:
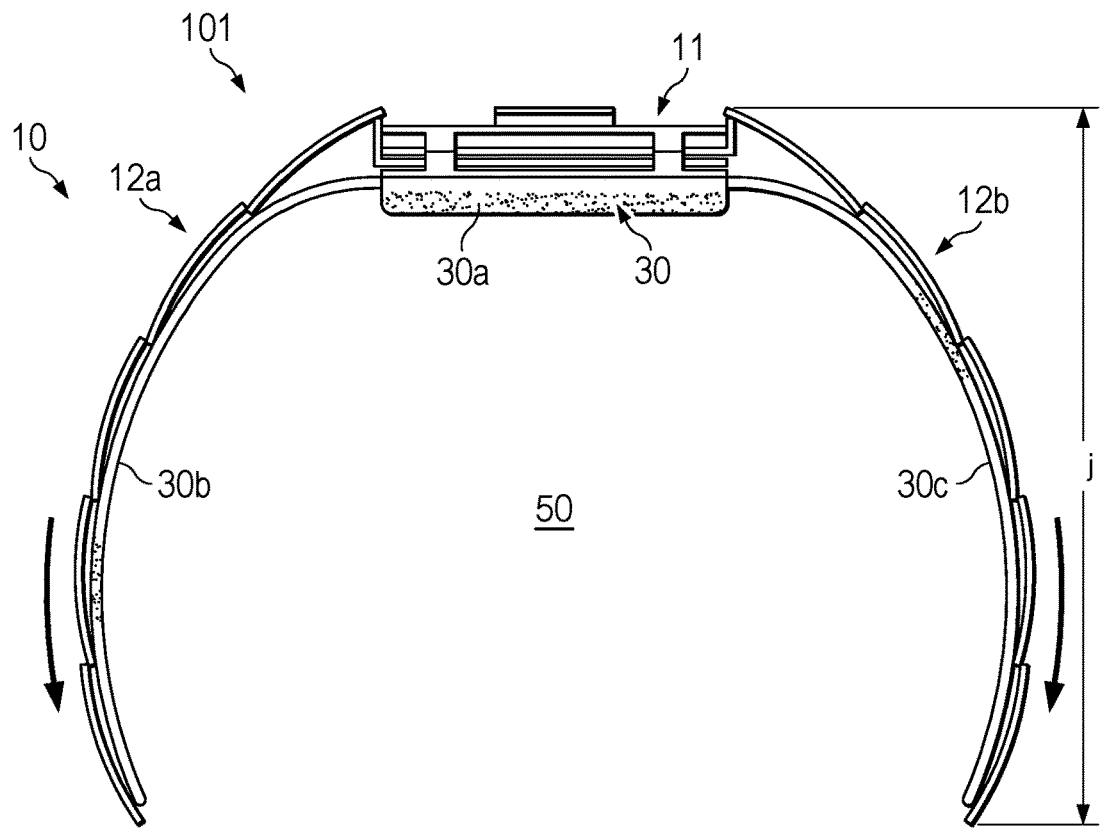
Figure 12B:
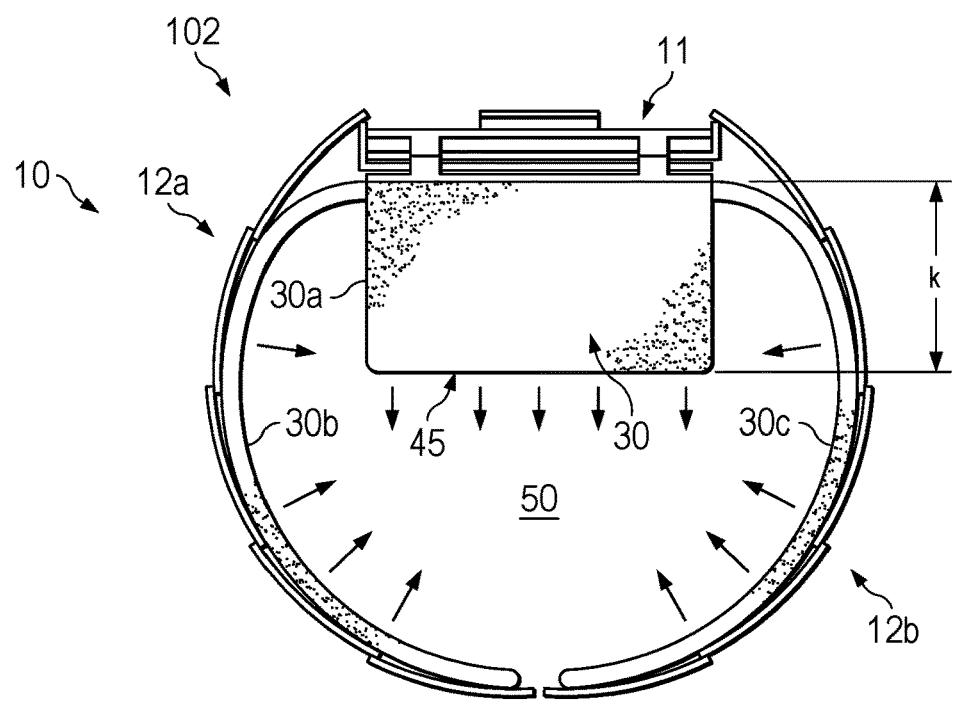

As shown in FIG. 12A, invention 10 has two primary states, an open or uncompressed state 101 and a closed or compressed state 102. Initially, invention 10 is manipulated to move segments 26,27 along arms 12a,b from a nested, collapsed state in which each segment is nested over one another and above base 11 (see FIG. 1), to an expanded uncompressed state 101. The invention may then be placed around a targeted treatment area and ratchet 17 actuated by rotating gear access 34 on base 11 with a T-handle wrench, or similar tool, or by a gear motor affixed to the topside of base 11 and engaged to ratchet via access 34. Ratchet 17 then retracts cable 29 causing each segment to move toward point 50, thereby surrounding and compressing against a targeted patient site. As compression increases, side bladder portion 30*b,c* cushion and apply pressure against a patient's extremity, thereby securing with substantial pressure the invention 10 over the patient while protecting the underlying tissue. Bladder 30 may then be either manually or automatically inflated to a full compression state 102 as shown in FIG. 12B. Bladder 30 is further inflated until fully extended into the space between arms 12*a,b* as shown toward point 50 and having a penetration depth of (k). This forces bladder tip 45 into a targeted patient area to occlude blood flow.

It will understood that various sensors and remote communications devices may be incorporated into base 11 so that compression of cable 29 and inflation of bladder 30 may be coordinated to best effect blood flow occlusion. It is anticipated that a remote field surgeon or medical technician would be able to operate the device 10 remotely, and monitor is operation, once the device is installed over a targeted area of a patient.

In operation, invention 10 may be used to in various treatment scenarios. For example, patients with serious injuries requiring initial medical/surgical stabilization may be helped with the invention. The invention also provides broad applicability to different hemorrhage situations, such as hemorrhage control for the extremities, junctional areas of the body (axilla, groin) and torso. These various tissue sites require a secure placement and compression of the underlying tissues which is accomplished by control of the mechanical base 11, ratcheting mechanism 17, and pneumatic bladder 30. The invention 10 also provides a stable platform for other medical interventions and diagnostic functions (i.e. vascular access, ultrasound imaging and percutaneous interventions to release air from a pneumothorax), as well as a platform for other advanced procedures that require anatomical precision. The device may be controlled by direct manipulation or by robotic control from a remote software application.

Having set forth the nature of the invention, what is claimed is:

1. A tourniquet, comprising:
   a. a baseplate;
   b. a pair of segmented arms depending downward from said baseplate;
   c. an airtight bladder depending downward from said baseplate, said bladder having integral side portions depending downward from said baseplate and along an underside of each said segmented arm; and,
   d. a cable wire system integrated into each downward depending segmented arm and controlled from a central spool held within said baseplate such that as cable wire is gathered up in said spool said pair of segmented arms compress inwards toward a central point below said baseplate.

2. A tourniquet as recited in claim 1, wherein each downward depending arm comprises a plurality of plate segments connected together in linear succession to form a segmented whole.

3. A tourniquet as recited in claim 2, wherein said baseplate further comprises a pair of extendable side plate portions biased together by an upper and lower plate portion, and wherein said pair of extendable plate portions are capable of moving from an enclosed position within said upper and lower plate portions to an extended position repositioned outward from opposing sides of said baseplate, and wherein each segmented arm is supported by one of said extendable side plate portions at a distal end thereof.

4. A tourniquet as recited in claim 3, wherein said cable wire system comprises a pair of cables running along the underside of each segmented arm, wherein each cable is affixed to each plate segment and connected to the central spool held by said baseplate.

5. A tourniquet as recited in claim 4, wherein said tourniquet is reconfigurable from an unfolded state to a compressed state wherein said cable wire system retracts said pair of cables to cause said segmented arms to compress towards one another and said bladder is inflated to cause at least a portion of said bladder to extend inwards between said compressed arms to apply constrictive force to a targeted human body portion.

6. A tourniquet as recited in claim 3, wherein said cable wire system comprises a pair of cables running through each segment in each segmented arm and further extending through a pair of tunnels extending from a proximal end to a distal end of each segment, wherein each cable is affixed to each segment and connected to the central spool held by said baseplate.

7. A tourniquet as recited in claim 2, wherein said bladder further comprises a central wedge-shaped portion depending downward from said baseplate in order to focus pressure on a lower edge of said bladder against a patient.

8. A tourniquet as recited in claim 2, further comprising inflation means connected to said bladder for inflation of said bladder.

9. A tourniquet as recited in claim 8, further comprising drive means for electrically driving said central spool.

10. A tourniquet as recited in claim 2, wherein said tourniquet is reconfigurable from a folded state wherein said pair of segmented arms fold into a nested set of plate segments adjacent to said baseplate to an unfolded state in which said pair of segmented arms expand into a pair of continuous arcuate segments depending downward from said based plate to form a semi-circular opposing pair.

11. A tourniquet as recited in claim 10, wherein said tourniquet is reconfigurable from an unfolded state to a compressed state wherein said cable wire system retracts said cable wire to cause said segmented arms to compress towards one another and said bladder is inflated to cause at least a portion of said bladder to extend inwards between said compressed arms to apply constrictive force to a targeted human body portion.

12. A tourniquet, comprising:
    a. a baseplate;
    b. means for providing a pair of downward depending arms extending away from opposing sides of said baseplate and curving inward toward one another;
    c. bladder means for expanding into a predefined airtight shape upon inflation; said bladder means configured for inflating downward from said baseplate with directed force toward a targeted area on a human patient;
    d. cable means coupled to said pair of depending arm means for drawing said depending arm means together; and,
    e. cable control means held by said baseplate for controlling the retraction of said cable means.

13. A tourniquet as recited in claim 12, wherein said tourniquet is reconfigurable from a folded state to an unfolded state, wherein said folded state comprises a nested pair of plate segments comprising said depending arm means and positioned adjacent to said baseplate, and wherein said unfolded state comprises said nested pair of plate segments unfolded into a pair of continuous arcuate segment chains depending downward from the sides of said baseplate to form a semi-circular opposing pair.

14. A tourniquet as recited in claim 13, wherein said tourniquet is reconfigurable from an unfolded state to a compressed state wherein said cable control means causes said cable means to retract causing said downward depending arm means to compress towards one another and said bladder means is inflated to cause at least a portion of said bladder means to extend inwards between said compressed arm means to apply constrictive force to a targeted human body portion.

15. A tourniquet as recited in claim 14, wherein said bladder means further comprises a central wedge-shaped portion depending downward from said baseplate in order to focus pressure on a lower edge of said bladder means against a patient.

16. A tourniquet as recited in claim 13, wherein said baseplate further comprises a pair of extendable side plate portions biased together by an upper and lower plate portion, and wherein said pair of extendable plate portions are capable of moving from an enclosed position within said upper and lower plate portions to an extended position repositioned outward from the sides of said baseplate, and wherein each downward depending arm means is supported by one of said extendable side plate portions at a distal end thereof.

17. A tourniquet as recited in claim 12, wherein each downward depending arm means comprises a plurality of plate segments connected together in linear succession to form a segmented whole.

18. A method for achieving homeostasis in a hemorrhaging human patient, comprising the steps of:
  a. unfolding a nested set of plate segments from around a baseplate to form a pair of expanded segmented arms depending downward from said baseplate;
  b. positioning said expanded arms and baseplate around a targeted hemorrhage area on a patient;
  c. retracting a cable connected to said segments in said depending arms so that said arms compress around said targeted area on said patient;
  d. inflating a bladder affixed to said baseplate causing a portion of said bladder to cover and compress said targeted area; and
  e. Continuing to inflate said bladder until blood vessel occlusion is caused in said targeted area.

19. The method as recited in claim 18, wherein said step of retracting a cable comprises the step of advancing a spool held in said baseplate so that said cable is retracted from each expanded arm causing inflection of each plate segment towards a centrally disposed point coincident with said targeted area.

20. The method as recited in claim 19, wherein said step of retracting a cable comprises the step of retracting a pair of cables running along an underside of each plate segment held by each segmented arm and terminated at a distal point at an end of each segmented arm.

21. The method as recited in claim 20, wherein said step of unfolding said nested set comprises the step of sliding a rail extending from the underside of each plate segment along a groove holding said rail within an adjacently positioned plate segment so that the relative position of each plate segment relative to an adjacently positioned plate segment moves from a staggered vertical orientation to a consecutive horizontal orientation.

22. The method as recited in claim 19, wherein said step of retracting a cable comprises the step of retracting a pair of cables running within a pair of tunnels traversing from one end of each plate segment to the other end distal said baseplate.

23. The method as recited in claim 18, wherein said step of unfolding said nested set comprises the step of sliding a rail extending from the underside of each plate segment along a groove holding said rail within an adjacently positioned plate segment so that the relative position of each plate segment relative to an adjacently positioned plate segment moves from a staggered vertical orientation to a consecutive horizontal orientation.

\* \* \* \* \*